United States Patent
Chien

(10) Patent No.: US 7,384,650 B2
(45) Date of Patent: *Jun. 10, 2008

(54) SKIN PERMEATION ENHANCEMENT COMPOSITION FOR TRANSDERMAL HORMONE DELIVERY SYSTEM

(75) Inventor: Te-Yen Chien, Neshanic Station, NJ (US)

(73) Assignee: Agile Therapeutics, Inc., Princeton, NJ (US)

( * ) Notice: Subject to any disclaimer, the term of this patent is extended or adjusted under 35 U.S.C. 154(b) by 612 days.

This patent is subject to a terminal disclaimer.

(21) Appl. No.: 10/621,711

(22) Filed: Jul. 17, 2003

(65) Prior Publication Data

US 2004/0053901 A1    Mar. 18, 2004

Related U.S. Application Data

(63) Continuation-in-part of application No. 10/130,913, filed as application No. PCT/US00/32043 on Nov. 22, 2000, now Pat. No. 7,045,145.

(60) Provisional application No. 60/167,535, filed on Nov. 24, 1999.

(51) Int. Cl.
  *A61F 13/02* (2006.01)
  *A61L 15/16* (2006.01)

(52) U.S. Cl. .................... 424/448; 424/449; 424/443

(58) Field of Classification Search ............... 424/448, 424/449, 443
See application file for complete search history.

(56) References Cited

U.S. PATENT DOCUMENTS

| | | | |
|---|---|---|---|
| 2,918,494 A | 12/1959 | Closson et al. ............ 260/541 |
| 2,964,546 A | 12/1960 | Miwa et al. ................ 260/415 |
| 4,818,540 A | 4/1989 | Chien et al. | |
| 4,883,669 A | 11/1989 | Chien et al. | |
| 4,906,169 A | 3/1990 | Chien et al. | |
| 5,023,084 A | 6/1991 | Chien et al. ................ 424/448 |
| 5,122,382 A | 6/1992 | Gale et al. | |
| 5,296,230 A | 3/1994 | Chien et al. ................ 424/448 |
| 5,458,885 A | 10/1995 | Muller et al. | |
| 5,560,922 A | 10/1996 | Chien et al. ................ 424/448 |
| 5,567,922 A | 10/1996 | Schmuck et al. ........... 181/284 |
| 5,645,855 A | 7/1997 | Lorenz | |
| 5,676,968 A | 10/1997 | Lipp et al. | |
| 5,686,097 A | 11/1997 | Taskovich et al. .......... 424/448 |
| 5,702,956 A | 12/1997 | Ying et al. .................... 437/8 |
| 5,762,956 A | 6/1998 | Chien et al. ................ 424/449 |
| 5,780,050 A | 7/1998 | Jain et al. | |
| 5,788,983 A | 8/1998 | Chien et al. ................ 424/449 |
| 5,876,746 A | 3/1999 | Jona et al. .................. 424/449 |
| 5,972,377 A | 10/1999 | Jona et al. | |
| 6,007,835 A * | 12/1999 | Bon-Lapillonne et al. .. 424/448 |
| 6,024,974 A | 2/2000 | Li | |
| 6,024,975 A | 2/2000 | D'Angelo et al. | |
| 6,071,531 A | 6/2000 | Jona et al. | |
| 6,689,379 B1 | 2/2004 | Bracht | |

FOREIGN PATENT DOCUMENTS

EP    1 242 012    9/2002

* cited by examiner

*Primary Examiner*—Isis A Ghali
(74) *Attorney, Agent, or Firm*—Drinker Biddle & Reath

(57) ABSTRACT

A transdermal hormone delivery system (THDS) is disclosed. The THDS is useful for control of fertility and as therapy for a variety of diseases and conditions treatable by robust delivery of progestin and estrogen hormones, particularly the progestin, levonorgestrel. The THDS comprises a backing layer, an adjoining adhesive polymer matrix comprising an effective amount of at least a progestin hormone, delivery of which is enhanced by one or more skin permeation enhancing agents present in pre-determined amounts. The THDS is capable of providing effective daily doses of progestin and estrogen hormones from a small surface area in contact with the skin, e.g., less than 20 square centimeters. Methods of fertility control and various types of hormone replacement therapy utilizing the THDS are also disclosed.

26 Claims, No Drawings

SKIN PERMEATION ENHANCEMENT COMPOSITION FOR TRANSDERMAL HORMONE DELIVERY SYSTEM

This is a continuation-in-part of U.S. application Ser. No. 10/130,913, filed May 23, 2002, issued as U.S. Pat. No. 7,045,145, which is a U.S. National Application of International Application No. PCT/US00/32043, filed Nov. 22, 2000, which claims benefit of U.S. Provisional Application 60/167,535, filed Nov. 24, 1999, the entire contents of each of which are incorporated by reference herein.

FIELD OF THE INVENTION

The present invention relates to hormone treatment for control of fertility and as therapy for a variety of diseases and conditions. Specifically, the invention provides formulations and methods of use in connection with a transdermal hormone delivery system for robust delivery of steroid hormones.

BACKGROUND OF THE INVENTION

Various scientific articles and patent publications are referenced herein to describe the state of the art to which this invention pertains. Each of these publications is incorporated by reference herein in its entirety.

Hormone therapy using synthetic estrogens and/or progestins is currently used to control fertility and for treatment or prevention of a variety of hormone-related conditions or deficiencies, including control of acne, treatment of endometriosis, induction or prevention of amenorrhea, supporting pregnancy and treatment of galactorrhea, among numerous others. Traditionally, combinations of synthetic estrogen and synthetic progestin have been used in the past in orally administered dosage forms. Though the combination of synthetic progestin and estrogen effectively suppresses ovulation, certain undesirable side effects are associated with this type of oral contraceptive. For instance, the incidence of thromboembolic and related vascular disorders, including stroke and myocardial infarction, is higher in women using oral contraceptives; the relative risk may be eleven times greater in users as compared to a control population. Further, the risk increases sharply in women over 35 years of age. Contraceptive use has also been associated with increased evidence of benign liver tumors and an increased risk of gallbladder disease. Additionally, fetal abnormalities may result if a woman continues to take the pill after becoming pregnant.

Transdermal hormone delivery offers many advantages and avoids certain disadvantages associated with oral contraceptives and hormone treatments. Specifically, transdermal rate-controlled drug administration avoids the variability in absorption and metabolism associated with oral therapy. It further provides continuity of drug administration, permitting the use of a pharmacologically active agent with short biological half-life. Moreover, there is less chance of over- or under-dosing on a transdermal regimen, and patient compliance with a multi-day easy-to-use transdermal regimen is superior to daily oral dosing.

It is, therefore, highly desirable to provide formulations and transdermal systems that permit 1) use of high levels of progestin, 2) use of either synthetic or natural estrogen, 3) use of a minimum number of dosage units for each menstrual cycle, and further that provide appropriate levels of progestin and estrogen hormones to fully ensure fertility control or other treatment goals with minimal or no production of undesired metabolic or chemical degradative products.

In recent years various transdermal contraceptive delivery systems for fertility control in females have been developed. U.S. Pat. No. 5,296,230 describes a transdermal fertility controlling polymer matrix dosage unit comprising a backing layer, a polymer layer adhered to the backing layer comprising microdispersed dosage amounts of estrogen and progestin hormones, and an adhesive layer. U.S. Pat. No. 5,560,922 discloses the delivery of a natural estrogen, 17 β-estradiol, or ethinyl estradiol or a combination thereof with an amount of natural progesterone or a progestin in a dosage unit comprising a backing layer and an adjoining polyacrylate adhesive polymer layer containing microreservoirs that release the hormones.

U.S. Pat. No. 5,788,983 discloses a transdermal polymer dosage unit, a backing layer and a reservoir layer, the reservoir layer having multiple regions that contact the skin during use and optionally contain difference pharmaceutical therapeutic agents providing a variable rate of absorption. U.S. Pat. No. 5,762,956 describes a transdermal contraceptive delivery device and a method of fertility control utilizing the device. The system comprises a backing layer, and an adhesive polymer matrix, which has dispersed therein hormones effective for controlling fertility, as well as a combination of three skin permeation enhancers at a specified relative weight ratio.

The above described transdermal delivery systems are deficient in their ability to deliver sufficient quantities of progestin, particularly levonorgestrel, either alone or in proper balance with a selected estrogen, for one or more of a variety of reasons. For instance, the systems described in U.S. Pat. Nos. 5,296,230, 5,560,922 and 5,788,983 comprise dosage units that are cumbersome in size, e.g., with surface area up to 100 $cm^2$. The dosage unit described in U.S. Pat. No. 5,762,956 is purportedly smaller, but the amount of progestin delivered is not robust.

Accordingly, there is a need in the art for a transdermal hormone delivery system, and drug-delivery formulations for use therein, that can reliably achieve high serum levels of hard-to-deliver progestins, such as levonorgestrel, and a desired profile of progestin and selected estrogen for contraception and other purposes, with minimal side effects. It is also desirable that the dosage unit is comfortably-sized, cosmetically unobtrusive and reliably adherent.

SUMMARY OF THE INVENTION

The present invention is directed to a skin permeation enhancer composition for enhancing the absorption through the skin of a steroid hormone, to hormone delivery formulations, to a transdermal hormone delivery system (THDS) comprising a backing layer and an adhesive polymer matrix which has dispersed therein at least one hormone effective for controlling fertility or for other hormone therapy, and to related compositions and methods. The hormone delivery formulation, which can be utilized in the adhesive polymer matrix of the THDS, comprises one or more skin permeation enhancers, as specified in detail herein, a humectant/plasticizer and a polymer. The relative and absolute amounts of the respective skin permeation enhancers in the THDS are adjusted for optimum hormone delivery by utilizing specified amounts of starting materials and by controlling process parameters for producing the THDS, such as drying time and temperature.

According to one aspect of the invention, a skin permeation enhancer composition is provided for use in fabricating a transdermal hormone delivery system for delivery of one or more of a progestin, estrogen or testosterone hormone. The composition comprises a combination of a pharmaceutically acceptable organic solvent (e.g., dimethyl sulfoxide), a fatty ($C_8$-$C_{20}$) alcohol ester of a hydroxy acid (e.g., lactic acid), a lower ($C_1$-$C_4$) alkyl ester of a hydroxy acid (e.g., lactic acid), and a $C_6$-$C_{18}$ saturated or unsaturated fatty acid, such as capric acid. In a preferred embodiment utilizing DMSO, a fatty alcohol ester of lactic acid, a lower alkyl ester of lactic acid and capric acid, the four excipients are combined in a weight ratio of 2:1:1:0.8 to 6:1:1:0.8, respectively, more specifically, 3:1:1:0.8 to 4:1:1:0.8, respectively. In specific embodiments, the fatty alcohol ester of lactic acid is lauryl lactate and the lower alkyl ester of lactic acid is ethyl lactate.

Another aspect of the invention features a polymer formulation for use in fabricating a transdermal hormone delivery system of a type comprising a backing layer and a polymer matrix, preferably an adhesive polymer matrix, in which is dispersed one or more of a progestin, estrogen or testosterone hormone to be transdermally delivered. This formulation comprises a polymer and, on a weight percentage basis, from about 0% to about 5% humectant/plasticizer, and from about 10% to about 30% of a skin permeation enhancer composition comprising a combination of a pharmaceutically acceptable organic solvent (e.g., dimethyl sulfoxide), a fatty ($C_8$-$C_{20}$) alcohol ester of a hydroxy acid (e.g., lactic acid), a lower ($C_1$-$C_4$) alkyl ester of a hydroxy acid (e.g., lactic acid), and a $C_6$-$C_{18}$ saturated or unsaturated fatty acid, such as capric acid. In a preferred embodiment utilizing DMSO, a fatty alcohol ester of lactic acid, a lower alkyl ester of lactic acid and capric acid, the four excipients are combined in a weight ratio of 2:1:1:0.8 to 6:1:1:0.8, respectively, more specifically, 3:1:1:0.8 to 4:1:1:0.8, respectively. Preferably the polymer is an adhesive polymer and, in certain embodiments, the adhesive polymer is a polyacrylate adhesive copolymer. More specifically, the polyacrylate adhesive copolymer comprises a 2-ethylhexyl acrylate monomer and further comprises about 3% to about 60% w/w vinyl acetate. In certain embodiments, the humectant/plasticizer is a polyvinylpyrrolidone/vinyl acetate. In certain embodiments, the fatty alcohol ester of lactic acid is lauryl lactate and the lower alkyl ester of lactic acid is ethyl lactate.

In certain embodiments of the invention, the polymer formulation comprises a progestin, which is levonorgestrel in preferred embodiments. The polymer formulation also may comprise a progestin and an estrogen, specifically levonorgestrel and ethinyl estradiol or 17 β-estradiol. An exemplary embodiment of this type of formulation comprises, on a weight percentage basis, about 79.65% polyacrylate adhesive copolymer, about 1.25% polyvinylpyrrolidone/vinyl acetate, about 9.51% dimethyl sulfoxide, about 3.10% lauryl lactate, about 3.10% ethyl lactate, about 2.39% capric acid, about 0.58% levonorgestrel and about 0.28% ethinyl estradiol. In other embodiments, the polymer formulation comprises a progestin, and estrogen and a testosterone. In yet other embodiments, the formulation comprises a testosterone alone.

Another aspect of the invention features a THDS comprising a backing layer that is substantially impermeable to skin permeation enhancing agents, and progestin and estrogen hormones to be delivered transdermally. The hormones are dispersed in an adhesive polymer matrix affixed to the backing layer. The adhesive polymer matrix is made from the adhesive polymer formulation described above. After fabrication of the THDS is complete, the adhesive polymer matrix comprises, on a final weight percentage basis of the adhesive polymer matrix: from about 0% to about 5% of a humectant/plasticizer; from about 12% to about 36% percent of a combination of skin permeation enhancing agents which is a mixture comprising from about 4% to about 12% of an pharmaceutically acceptable organic solvent, such as dimethyl sulfoxide, from about 4.2% to about 12.6% fatty ($C_8$-$C_{20}$) alcohol ester of hydroxy acid (e.g.,lactic acid), from about 0.7% to about 2.3% lower ($C_1$-$C_4$) alkyl ester of hydroxy acid (e.g., lactic acid), and from about 3% to about 9% $C_6$-$C_{18}$ fatty acid, such as capric acid; and an amount of one or more of the respective hormones effective to provide a pre-determined daily dose of each hormone for between about one and about nine days. In certain embodiments, the progestin is levonorgestrel and the estrogen is ethinyl estradiol or 17 β-estradiol. Alternative embodiments comprise adaptation of the THDS for delivery of (1) a progestin alone, (2) a testosterone in addition to the progestin and the estrogen, or (3) a testosterone alone.

In specific embodiments of the invention, the humectant/plasticizer is a polyvinylpyrrolidone/vinyl acetate. The adhesive copolymer comprises a polyacrylate copolymer, preferably one that comprises a 2-ethylhexyl acrylate monomer and further contains about 3 to 60% w/w vinyl acetate.

In addition to the specified amounts of skin permeation enhancers set forth above in the post-fabrication THDS, certain embodiments call for the enhancers to be present in a weight ratio of about 4-8 parts DMSO, about 4-8 parts fatty alcohol ester of lactic acid, about 1 part lower alkyl ester of lactic acid and about 3-6 parts capric acid. It is preferred that the DMSO and the fatty alcohol ester of lactic acid are present in a weight ratio of between about 1.5:1 and about 1:1.5.

In specific embodiments, the THDS is formulated for delivery of ethinyl estradiol and levonorgestrel, wherein the ethinyl estradiol is transdermally delivered at a rate of between about 10 µg and 50 µg per day for a term of about one day to about nine days, and the levonorgestrel is transdermally delivered at a rate of at least 20 µg per day, more specifically at least 30 µg per day, for a term of about one day to about nine days. In use, the THDS transdermally delivers sufficient levonorgestrel to produce a steady state serum concentration of at least 1,000 pg/ml.

A THDS of the invention is capable of robust delivery of progestin, estrogen and testosterone hormones, even from a comparatively small surface area. Accordingly, another aspect of the invention features a THDS comprising a backing layer and an adhesive polymer matrix, wherein the adhesive polymer matrix is of a maximum surface dimension of about 20 cm$^2$ and a maximum cross-sectional dimension of about 300 µm and is capable of delivering at least 20 µg/day, more preferably at least 30 µg/day, levonorgestrel for between about one and about nine days. In preferred embodiments the adhesive polymer maxtrix is of a maximum surface dimension of 17.5 cm$^2$ or 15 cm$^2$. In specific embodiments, the THDS is formulated for delivery of levonorgestrel and delivers an amount of levonorgestrel sufficient to impart a serum concentration of levonorgestrel of at least 1,000 pg/ml.

In other embodiments, the THDS is formulated for delivery of levonorgestrel and an estrogen, such as ethinyl estradiol or 17 β-estradiol. More specifically, the estrogen is ethinyl estradiol and is transdermally delivered at between 10 µg and 50 µg per day for between about 1 and about nine days.

The THDS of the invention is made by combining appropriate amounts of adhesive polymer, humectant/plasticizer, skin permeation enhancing agents and hormones, then coating the mixture onto the backing layer and drying the coated mixture at a pre-determined temperature for a pre-determined time. In an alternative embodiment, the adhesive polymer formulation is coated onto a piece of release liner. Starting amounts of ingredients and process parameters (e.g., coating thickness and drying time and temperature) are adjusted to arrive at the final weight ratios and weight percents of the respective skin permeation enhancing agents. Specifically, the method comprises: (1) preparing an adhesive polymer formulation by combining an adhesive copolymer solution with, on a weight percentage basis of the adhesive polymer formulation: from about 0% to about 5% of a humectant/plasticizer; from about 10% to about 30% percent of a combination of skin permeation enhancing agents which is a mixture comprising a pharmaceutically acceptable organic solvent, such as DMSO, a fatty ($C_8$-$C_{20}$) alcohol ester of a hydroxyl acid, such as lactic acid, a lower ($C_1$-$C_4$) alkyl ester of a hydroxyl acid, such as lactic acid, and a $C_6$-$C_{18}$ fatty acid, such as capric acid; and an amount of one or more of the selected hormones effective to provide a pre-determined daily dose of each hormone for between about one and about nine days, thereby forming an adhesive polymer matrix starting solution; (2) coating the adhesive polymer starting solution onto the backing layer; and (3) drying the coated backing layer for a time and at a temperature sufficient to produce a transdermal hormone delivery system as described above. In specific embodiments, the adhesive polymer starting formulation is coated onto the backing layer at a thickness of between about 300 μm and about 800 μm, the coated material dried for between about 5 minutes and about 25 minutes at a temperature between about 40° C. and about 80° C.

In certain embodiments, the THDS dosage unit is supplied with an overlay layer. The overlay layer may be affixed to the backing layer or it may be supplied separately, for application at the user's discretion. The overlay layer is coated with an adhesive and extends beyond the perimeter of part or all of the backing layer and adhesive polymer matrix. In an alternative embodiment, a non-adhesive polymer is substituted for the adhesive polymer, and skin adhesion is effected by the adhesive present in the overlay.

According to another aspect of the invention, a method of controlling fertility is provided, which comprises applying to the skin of a subject desiring such treatment a THDS as described above. The THDS is replaced once each week for three of four successive weeks of a menstrual cycle, for successive menstrual cycles extending as fertility control is desired. In specific embodiments, the THDS delivers levonorgestrel and an estrogen, preferably ethinyl estradiol or 17 β-estradiol. In other embodiments, the THDS is adapted for delivery of a progestin alone, preferably levonorgestrel.

In preferred embodiments, the method comprises transdermal delivery of ethinyl estradiol and levonorgestrel, wherein the ethinyl estradiol is delivered at a rate of between about 10 μg and 50 μg per day for a term of about one day to about nine days, and the levonorgestrel is delivered at a rate of at least 20 μg per day, preferably at least 30 μg per day, for a term of about one day to about nine days. In these embodiments of the method, the levonorgestrel is delivered in an amount sufficient to produce a blood concentration of at least 1,000 pg/ml, which exceeds required fertility-controlling serum levels.

The foregoing method is adaptable for individuals wishing to eliminate menses entirely. In this instance, the THDS is replaced once each week for consecutive weeks extending as fertility control and elimination of menses is desired.

In another adaptation, the THDS of the invention is formulated for delivery of testosterone alone. The THDS is used for treatment of deficiencies of circulating testosterone levels, resulting in decreased libido (both male and female), with the treatment comprising applying a THDS once each week for consecutive weeks extending as long as the treatment is desired.

Other features and advantages of the invention will be understood by reference to the detailed description and examples that follow.

DETAILED DESCRIPTION OF ILLUSTRATIVE EMBODIMENTS

Set forth below are various embodiments of the invention, including formulations used to make the adhesive polymer matrix of the THDS described herein, as well as process parameters for fabricating the THDS such that it can reliably achieve high serum levels of hard-to-deliver progestins, such as levonorgestrel, and a desired profile of progestin and selected estrogens and/or other hormones, for contraception and other purposes. These formulations and the THDS produced using these formulations differ from those currently disclosed or available, and constitute a significant advance in the art of transdermal hormone delivery. In one aspect, a THDS of the present invention comprises a progestin, most suitably levonorgestrel, and an estrogen, most suitably ethinyl estradiol or 17-β estradiol, dispersed in an adhesive polymer matrix affixed to a backing layer. In another aspect, the THDS comprises only a progestin. In other aspects, the THDS comprises a progestin, an estrogen and a testosterone, or a testosterone alone.

Dosage units of the THDS of the invention, sometimes referred to herein as "patches," in their most simple form comprise a backing layer to which is affixed an adhesive polymer matrix containing the hormones to be delivered and other excipients that facilitate the appropriate rate of transdermal delivery of those hormones. Briefly, the dosage units are made by combining the adhesive polymer, hormones and excipients into a starting formulation, coating that formulation onto the backing layer (or onto a release liner in an alternative embodiment), and drying the coated backing layer for a specific time, at a specific temperature, which is designed to produce a dosage unit in which the hormones and excipients are present in specific amounts that are optimum for the delivery of the hormones. For reasons described in detail herein, the amounts of respective components within the starting formulation are different from the amounts of components found in the final THDS after the fabrication process is complete. To distinguish these, the terms "adhesive polymer formulation," "adhesive polymer solution" or "starting solution" are used herein to refer to the starting formulation, prior to coating onto the backing layer and drying. The term "adhesive polymer matrix" is used herein to refer to the adhesive polymer solution after it has been coated onto the backing layer and dried (i.e., "post-fabrication").

Components of the Adhesive Polymer Formulation:

Skin Permeation Enhancers: Drug molecules released from a transdermal delivery system must be capable of penetrating each layer of skin. In order to increase the rate of permeation of drug molecules, a transdermal drug delivery system must be able in particular to increase the permeability of the outermost layer of skin, the stratum corneum, which provides the most resistance to the penetration of molecules. In this regard, the present invention provides a transdermal hormone delivery system that employs one or more skin permeation enhancers in specific amounts. It is the control of absolute and relative amounts of skin permeation enhancers that provides the sufficient flux of the penetrating hormones. The skin permeation enhancers also provide the desired permeation rate ratio of these hormones to achieve the desired amounts to be released from the transdermal contraceptive delivery system and delivered into the body to produce the desired effect.

A combination of skin permeation enhancing agents is preferably employed in the practice of the present invention. The combination comprises a mixture of (1) a pharmaceutically acceptable organic solvent, such as dimethyl sulfoxide (DMSO), (2) a fatty ($C_8$-$C_{20}$) alcohol ester of a hydroxy acid, such as lauryl lactate, (3) a lower ($C_1$-$C_4$) alkyl ester of a hydroxy acid, e.g., ethyl lactate, and (4) a $C_6$-$C_{18}$ fatty acid, such as capric acid. For optimum hormone delivery, these skin permeation enhancers are present at specified amounts within the adhesive polymer matrix, as set forth in detail below. In certain embodiments, one or more of the skin permeation enhancers may be eliminated from the polymer matrix. However the specific amounts of the remaining enhancers and their relative ratios in weight percent (in both the starting solution and the final dosage unit) should remain within the ranges set forth herein.

In a preferred embodiment, the pharmaceutically acceptable organic solvent is DMSO. Other organic solvents suitable for use in the present invention include, but are not limited to, $C_1$-$C_8$ branched or unbranched alcohols, such as ethanol, propanol, isopropanol, butanol, isobutanol, and the like, as well as azone (laurocapram: 1-dodecylhexahydro-2H-azepin-2-one) and methylsulfonylmethane, to name a few.

The fatty alcohol ester of hydroxy acid preferably is a fatty alcohol ester of lactic acid, such as lauryl lactate. However, other hydroxy acids and fatty alcohols may be utilized. Alternative hydroxy acids include, but are not limited to, alpha-hydroxy acids such as glycolic acid, tartaric acid, citric acid, malic acid and mandelic acid, as well as the beta-hydroxy acid, salicylic acid. Alternative fatty alcohols include any $C_8$-$C_{20}$ saturated or unsaturated fatty alcohol, such as myristyl, palmityl or oleyl alcohols, to name a few.

The lower alkyl ester of hydroxy acid also preferably utilizes lactic acid, and most preferably is ethyl lactate. However, other hydroxy acids, such as glycolic acid, tartaric acid, citric acid, malic acid, mandelic acid and salicylic acid, may also be utilized. In addition isopropylmyristic acid (IPM) may be used as a substitute for the lower alkyl ester of hydroxy acid.

The inventor has discovered that inclusion of a medium- to long-chain fatty acid in the skin permeation enhancer formulation improves the transdermal delivery profile of the hormones utilized in the present invention. Capric acid is preferred for use. However, other $C_6$-$C_{18}$ saturated or unsaturated fatty acids may be used, including but not limited to caproic acid, caprytic acid, lauric acid and myristic acid, to name a few.

The aforementioned combination of skin permeation enhancers may be used to enhance transdermal delivery of steroid hormones from any type of transdermal delivery device. An adhesive polymer matrix-type system as described in detail herein is preferred for use; however, the enhancer combination may also be utilized in non-adhesive polymers, as well as in multi-layer or reservoir-type transdermal delivery systems, to name a few.

Hormones: A THDS utilizing the aforementioned skin permeation enhancers can be used to deliver any type of hormone capable of transdermal delivery. More specifically, a THDS of the invention is formulated for delivery of animal steroid hormones. In one embodiment, a combination of a progestin and an estrogen is utilized for one or more of the following purposes: (1) control of fertility, (2) control of acne, (3) treatment of endometriosis, and (4) induction of amenorrhea. In another embodiment, a progestin alone is utilized for one or more of the following purposes: (1) control of fertility, (2) supporting pregnancy, (3) as an alternative hormonal therapy for individuals for whom estrogen is contra-indicated (e.g., lactating females), and (4) preventing galactorrhea. In still another embodiment, a combination of progestin, estrogen and testosterone is utilized as a hormone replacement therapy for the treatment of deficiency of these hormones in females. Yet another embodiment is directed to a THDS formulated for delivery of testosterone alone, which is useful for the treatment of decreased libido resulting from testosterone deficiency in both males and females.

A THDS of the invention comprising levonorgestrel is preferred for both combination hormone delivery and progestin-alone delivery. Levonorgestrel is known to be recalcitrant to transdermal delivery; however, the hormone is effectively delivered from the THDS of the present invention. With the controlled release of the hormone at a relatively steady rate over a prolonged period, typically several days and preferably one week to nine days, the subject is provided with the benefit of a steady infusion of hormones over a prolonged period.

Levonorgestrel is a potent progestin on a weight-dose basis, which is an important factor since the progestins often exhibit a much lesser degree of transdermal absorption than do the estrogens. Other progestins that could be used in part or total are norgestrel, norgestimate, desogestrel, gestodene, norethindrone, nore-thynodrel, hydrogesterone, ethynodiol dicetate, hydroxyprogesterone caproate, medroxyprogesterone acetate, norethindrone acetate, progesterone, megestrol acetate, gestogen and certain others which are biocompatible and absorbable transdermally. These include biocompatible derivatives of progestins that are transdermally absorbed, some of which, advantageously, are bioconvertible after transdermal absorption to the original progestin. The progestin and other hormones selected should have high compatibility with each other.

For combinations of progestin with estrogen, the synthetic hormone ethinyl estradiol is particularly suitable. This hormone may be transdermally delivered in conjunction with the particularly suitable progestin, levonorgestrel, by a TDHS of the present invention at desirable daily rates for both hormones. Ethinyl estradiol and levonorgestrel are compatible and can be dispersed in the adhesive polymer formulation. Typically, a transdermal dosage unit designed for one-week therapy should deliver at least about 20 μg/day of levonorgestrel (or an equivalent effective amount of another progestin) and 10-50 μg/day of ethinyl estradiol (or an equivalent effective amount of another estrogen). Those respective amounts of progestin and estrogen are believed to be necessary to inhibit ovulation and to maintain normal female physiology and characteristics. In the present invention, the amount of levonorgestrel transdermally delivered is preferably 30 μg per day for more than one day to about one week with a 15 $cm^2$ transdermal delivery device.

Derivatives of 17 β-estradiol that are biocompatible, capable of being absorbed transdermally and preferably bioconvertible to 17 β-estradiol may also be used, if the amount of absorption meets the required daily dose of the estrogen component and if the hormone components are compatible. Such derivatives of estradiol include esters, either mono- or di-esters. The monoesters can be either 3- or 17-esters. The estradiol esters can be, illustratively speaking, estradiol-3, 17-diacetate; estradiol-3-acetate; estradiol 17-acetate; estradiol-3, 17-divalerate; estradiol-3-valerate; estradiol-17-valerate; 3-mono-, 17-mono- and 3,17-dipivilate esters; 3-mono-, 17-mono- and 3,17-dipropionate esters; 3-mono-, 17-mono- and 3,17-dicyclo pentyl-propionate esters; corresponding cypionate, heptanoate, benzoate and the like esters; thinyl estradiol; estrone; and other estrogenic steroids and derivative thereof that are transdermally absorbable.

Combinations of the above with estradiol itself (for example, a combination of estradiol and estradiol-17-valerate or further a combination of estradiol-17-valerate and estradiol-3, 17-divalerate) can be used with beneficial results. For example, 15-80% of each compound based on the total weight of the estrogenic steroid component can be used to obtain the desired result. Other combinations can also be used to obtain desired absorption and levels of 17 β-estradiol in the body of the subject being treated.

Formulations comprising testosterone may utilize natural testosterone or synthetic testosterones that are absorbed transdermally. For instance, methyl testosterone is suitable for use in the present invention. In premenopausal women, the rate of testosterone production is about 300 μg/day. Accordingly, THDS for testosterone delivery should be formulated for delivery of an amount of testosterone to supplement a partial or total deficiency, i.e., up to about 300 μg daily. Likewise, for treatment of testosterone deficiency in males, THDS should be formulated to deliver up to about 3-6 mg daily.

It will be appreciated that the hormones may be employed not only in the form of the pure chemical compound, but also in admixture with other pharmaceuticals that may be transdermally applied or with other ingredients which are not incompatible with the desired objective as listed above. Thus, simple pharmacologically acceptable derivatives of the hormones such as ethers, esters, amides, acetals, salts and the like, if appropriate, may be used. In some cases, such derivatives may be preferred. The progestin compound and the estrogenic steroid are ordinarily dispersed or dissolved concurrently in fabricating the hormone-containing adhesive polymer matrix or they may be dispersed or dissolved separately.

Adhesive Polymer: Generally, polymers used to form the biologically acceptable adhesive polymer matrix are those capable of forming thin films or coatings through which hormones can pass at a controlled rate. Suitable polymers are biologically and pharmaceutically compatible, nonallergenic, insoluble in and compatible with body fluids or tissues with which the device is contacted. The use of soluble polymers is to be avoided since dissolution or erosion of the matrix would affect the release rate of the hormones as well as the capability of the dosage unit to remain in place for convenience of removal.

Suitable materials for the adhesive polymer formulation include polyethylene, polypropylene, ethylene/propylene copolymers, ethylene/ethyl acrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylenevinyloxyethanol copolymers; silicone copolymers, for example, polysiloxanepolycarbonate copolymers, polysiloxanepolyethylene oxide copolymers, polysiloxane-polymethacrylate copolymers, polysiloxane-alkylene copolymers (e.g., polysiloxane-ethylensilane copolymers), and the like; cellulose polymers, for example methyl or ethyl cellulose, hydroxypropyl methy cellulose, and cellulose esters; polycarbonates; polytetrafluoroethylene; and the like.

Preferably, the adhesive polymer should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers that can be incorporated into polyacrylate polymers include polymethacrylic esters of polyols such as butylene diacrylate and dimethacrylate, trimethylol propane trimethacrylate and the like. Other monomers that provide such sites include allyl acrylate, allyl methacrylate, diallyl maleate and the like.

Preferably, the adhesive polymer formulation comprises a polyacrylate adhesive polymer of the general formula (I):

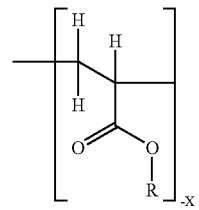

wherein x represents the number of repeating units sufficient to provide the desired properties in the adhesive polymer and R is H or a lower ($C_1$-$C_{10}$) alkyl, such as ethyl, butyl, 2-ethylhexyl, octyl, decyl and the like. More specifically, it is preferred that the adhesive polymer matrix comprises a polyacrylate adhesive copolymer having a 2-ethylhexyl acrylate monomer and approximately 50-60% w/w of vinyl acetate as a co-monomer. An example of a suitable polyacrylate adhesive copolymer for use in the present invention includes, but is not limited to, that sold under the tradename of DURO TAK 87-4098 by National Starch and Chemical Co., Bridgewater, N.J., which comprises a certain percentage of vinyl acetate co-monomer.

Humectant/plasticizer: Preferably, a plasticizer/humectant is dispersed within the adhesive polymer formulation. Incorporation of a humectant in the formulation allows the dosage unit to absorb moisture on the surface of skin which in turn helps to reduce skin irritation and to prevent the adhesive polymer matrix of the delivery system from failing. The plasticizer/humectant may be a conventional plasticizer used in the pharmaceutical industry, for example, polyvinyl pyrrolidone (PVP). In particular, PVP/vinyl acetate co-polymers, such as those having a molecular weight of from about 50,000, are suitable for use in the present invention. The PVP/vinyl acetate acts as both a plasticizer, acting to control the rigidity of the polymer matrix, as well as a humectant, acting to regulate moisture content of the matrix. Preferably, the PVP/vinyl acetate is PVP/VA S-630 supplied by International Specialty Products, Inc. (ISP) of Wayne, N.J., wherein the PVP and the vinyl acetate are each present in approximately equal weight percent.

Backing Layer: The backing layer can be made of any suitable material that is impermeable to the hormones and other excipients of the adhesive polymer matrix. The backing layer serves as a protective cover for the matrix layer and provides a support function. The backing layer can be formed so that it is essentially the same size as the hormone-containing adhesive polymer matrix or it can be of larger dimension so that it can extend beyond the sides of the adhesive polymer matrix outwardly so that the surface of the extension of the backing layer can be the base for an adhesive overlay, as described in greater detail below. The backing layer can be any appropriate thickness that will provide the desired protective and support functions. A suitable thickness is from about 10 to about 300 microns. More specifically, the thickness is less than about 150 microns, yet more specifically, it is less than about 100 microns, and most specifically, the thickness is less than about 50 microns.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Polyester films, such as Scotchpak® 9732 (3M Company), are particularly suitable for use in the present invention.

Preparation of Adhesive Polymer Formulation: In accordance with the present invention, THDS dosage units are made with attention to the concentration of ingredients within the patch at completion of the fabrication process. Accordingly, parameters that may be varied to achieve the appropriate final amounts and ratios of ingredients include the starting formulation, as well as the process parameters utilized to fabricate the patch, as described below.

In making the hormone-containing adhesive polymer formulation, polyacrylate adhesive polymers of the formula described above are preferably utilized. The hormones are added in an amount determined by the hormone dosage and the duration of treatment desired in each dosage unit.

Generally speaking, it is preferred that the starting formulation comprises between about 10 and about 30 percent of skin permeation enhancer combination based on the weight of the adhesive polymer starting solution. More preferably, about 13 to 27%, yet more preferably about 16-24% or even more preferably, about 19-21% of skin permeation enhancer combination is used, based on the weight of the adhesive polymer starting solution. In preferred embodiments, the skin permeation enhancers are formulated within the adhesive polymer starting solution at a weight ratio (weight % of the adhesive polymer matrix) of:2:1:1:0.8 to 6:1:1:0.8, of DMSO, fatty alcohol ester of lactic acid, lower alkyl ester of lactic acid, and capric acid, respectively. More specifically, the ratio is 3:1:1:0.8 to 4:1:1:0.8. These weight ratios are particularly suitable for THDS fabricated using process parameters comprising coating the adhesive solution onto the backing layer at a thickness between 500 μm and 700 μm and drying at about 60° C. for about 15 minutes.

As can be seen from the data presented in Examples 1-3, differential gains/losses of the various skin permeation enhancers occur during the process of fabricating the THDS. For instance, under the process parameters set forth in Examples 1-3, the weight percent of DMSO in the post-fabrication adhesive polymer matrix is between about 65 and 90% of the amount added to the starting formulation. Likewise, ethyl lactate decreases to about 50-75% of its initial amount. In contrast, the final amount of lauryl lactate is about 2.6 to four-fold greater than the starting percentage and capric acid similarly increases to about 2.5-3.9-fold its initial starting percentages. These differential changes likely result from an overall decrease in volume of the post-fabricated matrix, combined with differences in volatility of the respective skin permeation enhancers. Regardless of the underlying reasons for the observed changes, the amounts of respective enhancers in the starting formulation should take into account the differential gains or losses that occur during processing. One of skill in the art would be capable of making the appropriate adjustments for starting materials, utilizing the information provided herein as well as information commonly available to pharmaceutical and medicinal chemists.

It is preferred that the hormone-containing adhesive polymer matrix contains some excess of the dispersed hormone over the dosage amount desired to be delivered. To accomplish this, the starting formulation can comprise an excess of hormone of about 5.0 to about 50 times the desired dosage. More preferably, the excess is about 10 to about 25 times the desired dosage to be transdermally absorbed.

In THDSs formulated for delivery of an estrogen and a progestin, it is preferred that the starting formulation comprise a ratio of progestin to estrogen of at least about 1.8:1, yet more preferably about 2:1. While not intending to be bound by any particular mechanism of action, it is believed that the inclusion of a lesser amount of estrogen increases the amount of free progestin in the blood because estrogen is known to induce the production of sex hormone binding globulin, which binds progestin. For this reason, not only is the ratio of progestin to estrogen believed to be significant, but also the total amount of estrogen in the formulation preferably is kept to a minimum, e.g., less than about 0.3% by weight of the starting adhesive polymer formulation as described herein.

Depending upon the hormones utilized and the drug delivery desired, a suitable amount of a plasticizer can be varied from zero to about 10 percent, based on the weight of the adhesive polymer matrix. Preferably, the amount of humectant/plasticizer present in the final dosage unit is less than 5%. When PVP/vinyl acetate is used, it can be added as an aqueous solution with the PVP/vinyl acetate content varying from 0.5 to about 5 percent, based on the weight of the final dried matrix of the patch, noting that the weight percent of the humectant/plasticizer is greater in the final product as compared with the starting formulation.

Example 1 sets forth an exemplary starting formulation of the invention. This formulation is suitable for use with the preferred fabrication process parameters set forth below.

Preferably, prior to mixing with adhesive polymer, the hormones used are dissolved and dispersed in a solution comprising the plasticizer and the combination of skin permeation enhancers. More preferably, the enhancer combination and the plasticizer solution are combined, the hormones added thereto and subjected to mixing.

Typically, the adhesive polymer solution is added to the solution of hormones dispersed in the enhancer combination/plasticizer solution. The mixture of adhesive polymer and the plasticizer/enhancer/hormone solution is then thoroughly mixed using a high-torque mixer to form a homogeneous dispersion or solution of the hormones in the adhesive polymer. The mixed solution is then allowed to stand undisturbed until deaerated, e.g., for a time period of at least one hour up to 24 hours.

Fabrication of THDS Dosage Units: Once deaerated, the adhesive polymer solution is applied to the backing layer material, and subsequently dried for a set time at a set temperature. In an alternative embodiment, the adhesive polymer matrix may be applied to a release liner instead of to the backing layer. Accordingly, reference herein to application of the adhesive polymer matrix to the backing layer will be understood to include this alternative embodiment. Application of the deaerated adhesive polymer matrix to the backing layer may be accomplished using commercially available laboratory coating/drying apparatus routinely used for this purpose. For instance, the Werner Mathis Model LTSV/LTH apparatus may be utilized, as well as other laboratory coating devices available from Werner Mathis AG (Zurich, Switzerland). Other suitable devices include, but are not limited to, instruments produced by Cheminstruments, Inc. (Cincinnati, Ohio).

The thickness of the adhesive polymer solution applied to the backing layer, as well as the time and temperature of drying, are all process parameters that can be varied to achieve the final concentrations and ratios of hormones and permeation enhancing agents within the patch. For instance, as described in greater detail in Example 3, it has been found that a change in the thickness of adhesive polymer matrix applied to the backing layer (e.g., from 300 to 800 μm) results in an overall greater retention of skin permeation enhancers when the other two process parameters, drying time and drying temperature, are held constant. In contrast, changing the drying time, e.g., from 5 to 25 minutes, or the drying temperature, e.g., from 40-100° C., results in overall losses in retention of skin permeation enhancers, to a greater or lesser degree depending on the enhancer.

Thus, it will be appreciated by those of skill in the art that, in addition to selection of appropriate amounts of starting materials in the adhesive polymer starting formulation, an appropriate combination of (1) initial thickness of the deaerated adhesive polymer solution spread on the backing layer, (2) drying time and (3) drying temperature may be selected to achieve the final composition of skin permeation enhancers and hormones in the THDS, as set forth below. A suitable initial thickness of the deaerated adhesive polymer matrix can range from 300 to 800 μm, more specifically from 400 or 500 to 700 μm, with an average thickness being about 600-700 μm. A suitable drying time should be at least five minutes, but can range to 10, 15, 20, 25 or more minutes, depending on the other process parameters chosen. Likewise, a suitable drying temperature ranges from room temperature to 40, 50, 60, 70 or 80° C., again depending on the process parameters chosen. In preferred embodiments, the initial thickness of the coated solution is about 500-700 μm, more preferably 600-700 μm; the drying temperatures is about 50-80° C., more preferably 55-65° C., yet more preferably about 60° C.; and the drying time is about 10-20 minutes, more preferably about 15 minutes. An exemplary embodiment of the invention utilizes an initial coating thickness of 600-700 μm, a drying temperature of 60° C. and a drying time of 15 minutes.

After the fabrication process is finished, the total amount of enhancer mixture in the dried adhesive polymer matrix is about 12-36% w/w of the polymer matrix, more specifically between about 15 and 33%, yet more specifically between about 18 and 30%, even more specifically between about 21 and 27%, most specifically about 23-25% w/w, especially when an acrylate copolymer is used.

Post fabrication, the THDS of the invention also comprises specified amounts of individual skin permeation enhancers on a weight basis of the adhesive polymer matrix, which differ from the pre-drying amounts for the reasons set forth above. Thus, in the dried adhesive polymer layer, DMSO comprises between about 4% and 12% by weight of the polymer matrix, more specifically between about 5% and 11%, yet more specifically about 6-10%, even more specifically about 7-9%, and most specifically about 8% by weight of the adhesive polymer matrix. The fatty alcohol ester of lactic acid comprises between about 4.2% and 12.6% by weight of the polymer matrix, more specifically between about 5.2% and 11.6%, yet more specifically about 6.2-10.6%, even more specifically about 7.2-9.6%, and most specifically about 8.4% by weight of the adhesive polymer matrix. The lower alkyl ester of lactic acid comprises between about 0.7% and 2.3% by weight of the polymer matrix, more specifically between about 1.0% and 2.0%, yet more specifically about 1.2-1.8%, and most specifically about 1.5% by weight of the adhesive polymer matrix. The capric acid comprises between about 3% and 9% by weight of the polymer matrix, more specifically between about 4% and 8%, yet more specifically about 5-7%, and most specifically about 6% by weight of the adhesive polymer matrix.

Post-fabrication, it is also preferred that the skin permeation enhancers be present in the adhesive polymer matrix at a weight ratio as follows: for each part of lower alkyl ester of lactic acid, about 4-8 parts DMSO, about 4-8 parts fatty alcohol ester of lactic acid and about 3-6 parts capric acid. Stated another way, the typical ratio is (4-8):(4-8):1:(3-6) of DMSO: fatty alcohol lactate ester:lower alkyl lactate ester: capric acid. In preferred embodiments utilizing lauryl lactate as the fatty alcohol lactate ester and ethyl lactate as the lower alkyl lactate ester, the weight ratio of DMSO to lauryl lactate is held at between about 1:1.5 and 1.5:1, with an approximate 1:1 ratio being advantageous.

The dried adhesive polymer matrix is next laminated with a piece of release liner (such as Scotchpak® 1022 or 9744, 3M Co., St. Paul Minn.) (or backing layer, if the alternative embodiment is utilized), preferably of the same size to form a sheet of the transdermal hormone delivery systems. The resulting sheet can be cut to form discs or squares and the like, with desired shapes and sizes using a steel rule die and a hydraulic press. The discs or squares generally should not exceed about 60 cm$^2$ in area. Preferably, the discs or squares will be about 5 to 50 cm$^2$, more preferably, about 8 to about 40 cm$^2$. Most preferably, the discs will be about 10 to about 20 cm$^2$. A disc of 15 cm$^2$ is preferred because of its, relatively small size, yet being capable of dispersing high levels of hormones. Specific embodiments of the invention feature patches having a surface area of 10, 12.5, 15, 17.5 or 20 cm$^2$. However, other sizes may be utilized. An advantage of the THDS of the present invention is that it can be fabricated with thin, translucent materials, such as the Scotchpak® 9732 backing layer exemplified herein. The small size and unobtrusive appearance of the patch are cosmetically appealing to the user.

In a preferred embodiment of the invention, the THDS patches are adapted with an overlay film, which also may be selected from a variety of thin, preferably translucent films available in the art. In one embodiment, the overlay is designed to extend beyond the perimeter of the patch in all directions, typically by a margin of about 0.1 to 1.0 cm, more specifically about 0.3 to 0.7 cm, and yet more specifically about 0.5 cm beyond the perimeter of the patch. In an alternative embodiment, the overlay is designed to extend partially beyond the edge of the patch, i.e., forming "tabs" of overlay material that extend beyond the edges of the patch. The overlay may be fabricated with the other elements of the THDS, i.e., it may be affixed to the backing layer during fabrication of the THDS. Alternatively, the overlay may be fabricated separately, e.g., with its own releasable liner, in a separate pouch, such that the overlay may be applied at the discretion of the user. Overlay systems are commonly utilized in patches and other dermal devices, and may be prepared according to any standard methodology.

Though patches without overlays are suitable for use in accordance with the present invention, a patch comprising an overlay offers the advantage of more secure adherence of the THDS for the duration of its application (typically one week). Additionally, in a THDS without an overlay, the perimeter of the patch can be tacky from the adhesive polymer matrix, which extends to the very edge of the patch. The tacky perimeter can accumulate dirt, clothing lint and the like from the external environment, resulting in a cosmetically unappealing "dark ring" appearance at the edge of the patch. In an overlay-style patch, the THDS perimeter is shielded from the external environment by the overlay and the perimeter of the overlay exposes a much thinner edge to the external environment (e.g., about 75-100 μm combined thickness of overlay film and adhesive in a preferred embodiment). This minimizes the accumulation of external material onto the patch, and the "dark ring" is substantially avoided—constituting another cosmetic advantage of the overlay-style system.

The resulting THDS dosage units, prepared with or without overlay, are then placed in appropriate packaging for storage, such as paper and/or foil pouches, until they are to be applied in transdermal treatment.

Because of the importance of final absolute and relative amounts of skin permeation enhancers in the THDS patches, if one or more of the foregoing formulation or process parameters is varied, an important final step in the fabrication process is to quantitate these ingredient amounts after the process has been completed. This may be accomplished according to standard analytical techniques well known in the art, e.g., solvent extraction of components followed by liquid or gas chromatography. Examples of suitable methods are set forth in Example 2.

Methods of Use: The THDS of the invention employs the general method of applying a patch to the skin of a subject for a pre-determined amount of time commensurate with the particular condition being treated. The subject is typically a mammal and most typically a human, although the invention can be practiced on animals for various veterinary purposes. Typically, though this need not be the case, patches are formulated to deliver an effective amount of one or more hormones to achieve the desired effect, for a period of between 1 and 7-9 days. For continual hormone delivery, the patch is replaced with a fresh patch before depletion of the hormone(s) therein below the effective amount. In a typical course of ongoing treatment, the patch is replaced once weekly.

Fertility control in women is a preferred use of the THDS of the present invention. For a contraceptive system employing a progestin and an estrogen, the THDS of the present invention provides an increased rate of hormone release, thereby providing a high rate of delivery of the hormones. The levels of levonorgestrel capable of being delivered by the THDS of the invention exceed the level of about 1,000 pg/ml needed for contraception. Indeed, levels of over 1500-2000 pg/ml are reached with the system of the present invention (see Example 4). Further, the serum levels of ethinyl estradiol range from about 20-80 pg/ml, thereby providing effective support of the endometrium. Appropriate serum levels of hormones may be obtained by using a relatively small patch as mentioned above, preferably 10 to 20 $cm^2$, specifically 10, 11, 12, 13, 14, 15, 16, 17, 18, 19 or 20 (or intermediate increments, such as 12.5 or 17.5 for example) $cm^2$ in area, which enhances the convenience to the user.

Under certain conditions (e.g., other health conditions mandate against estrogen use), fertility may be controlled using a progestin alone. Levonorgestrel is often preferred for use, but transdermal delivery of sufficient amounts of levonorgestrel has been problematic heretofore. The THDS of the present invention is particularly advantageous in this regard, given the high serum concentrations of levonorgestrel that can be achieved through its use. For fertility control without estrogen, a continuous serum level of 300 pg/ml has been found effective in subcutaneous levonorgestrel implants. This serum level is easily achievable using the THDS of the invention.

Regimens for transdermal administration of hormones for control of fertility are well known. Patches are usually formulated to deliver fertility-controlling amounts of the hormone(s) for a period of between 1 and 7-9 days. In a typical regimen comprising a 28-day cycle, the patch is replaced once weekly for three weeks. On the fourth week, no patch is worn, or a placebo patch may be worn.

In an alternative regimen, a patch may be worn on the fourth week, thus providing a continuous transdermal supply of the hormones. This regimen may be utilized by women who wish to avoid menses entirely. It may be continued indefinitely or terminated after a few months (e.g., 3, 4 or 6 months).

The THDS of the invention may be utilized for indications other than fertility control. For instance, estrogen/progestin combinations in fertility-controlling amounts have also been utilized for control of acne, control of symptoms of endometriosis and induction of amenorrhea. THDSs formulated with progestin (e.g., levonorgestrel) alone in fertility-controlling amounts may also find utility to support pregnancy and for use in individuals for whom estrogen is contra-indicated (e.g., women at risk of breast cancer), as well as for inhibition of galactorrhea, which is the secretion of breast milk in men or non-breastfeeding women.

The THDS of the present invention offers many advantages over transdermal hormone and contraceptive systems currently available. As discussed in detail above, the primary advantage comprises delivery of high amounts of fertility-controlling hormones, particularly levonorgestrel, from a relatively small surface area patch, which may be manufactured from backing and overlay materials that are thin and translucent, thereby increasing their cosmetic acceptability. These features add to the utility and desirability of the THDS of the invention for the multiple purposes described herein. Furthermore, breast tenderness and engorgement often associated with such therapies have been found to be markedly reduced in patients using the THDS of the present invention, as compared with other systems, as has incidence of nausea and/or vomiting.

The following examples are set forth to describe the invention in greater detail. They are intended to illustrate, not to limit, the invention.

EXAMPLE 1

| Fabrication of THDS Dosage Units for Use in Contraception | | |
|---|---|---|
| Materials: | mg | wt % |
| Humectant PVP/VA-S630: | 9.66 | 1.25 |
| Skin permeation enhancers: | | |
| DMSO | 73.77 | 9.51 |
| Lauryl lactate (Ceraphyl ® 31) | 24.59 | 3.10 |
| Ethyl lactate | 24.59 | 3.10 |
| Capric Acid | 18.54 | 2.39 |
| Adhesive polymer: | 617.59 | 79.65 |
| DURO TAK 87-4098 | | |
| Hormones: | | |
| Levonorgestrel | 4.48 | 0.58 |
| Ethinyl estradiol | 2.20 | 0.28 |
| Backing layer - Scotchpak ® 9732 (3M Company) | 16 sheets | — |
| Release liner - Scotchpak ® 1022 (3M Company) | 16 sheets | — |
| TOTAL | 775.41 mg | 100.00% |

Process:

Hormones were dissolved and dispersed in a solution comprising PVP/vinyl acetate and the combination of skin permeation enhancers. DURO TAK 87-4098 (33% solid content) adhesive polymer solution was added, and the container was sealed. The solution was stirred using a magnetic stirring bar at approximately 200 rpm at room temperature for 3 hours, to form a homogeneous solution. The stirred solution was deaerated by allowing it to stand without stirring for one hour or until all air bubbles had disappeared. The deaerated solution was coated onto a piece of the backing layer to a thickness of 700 μm, then dried at 60° C. for 15 minutes, using a laboratory coating/drying machine (Model LTSV/LTH, Werner Mathis, Switzerland). The dried adhesive polymer matrix was laminated with a piece of release liner of the same size as the backing layer, to form a sheet of THDS. The sheets were cut into dosage units of 15 cm$^2$ using a steel rule die and hydraulic press at 4000 psi. Each dosage unit was individually packaged in a paper or foil pouch and stored at 4° C.

EXAMPLE 2

Quantitative Analysis of Dried Adhesive Polymer Matrix

The THDS dosage units fabricated as described in Example 1 were subjected to quantitative analysis to determine the post-fabrication amounts of each component. Amounts of levonorgestrel (LNG) and ethinyl estradiol (EE) were measured as follows. A dosage unit was taken from its foil pouch and the release liner was removed. The dosage unit was folded together on the adhesive side and placed into an extraction container, to which 100 ml of methanol was added. The container was shaken vigorously by hand, then placed on an orbital shaker for at least 12 hours, until all adhesive on the dosage units was dissolved. Twenty-one ml of the extracted solution was placed into a centrifuge tube, and 9 ml of HPLC-grade water was added, to yield an aqueous methanol solution composed of 70% methanol. The sample was centrifuged and the supernatant filtered through a 0.45 μm (nylon or Teflon) filter paper into an HPLC vial. The filtrate was injected into a high pressure liquid chromatograph with UV monitor.

Amounts of other excipients were measured as follows. A dosage unit was taken from its foil pouch and the release liner was removed. The dosage unit was folded together on the adhesive side cut into pieces and placed into an extraction container, to which 2 ml of tetrahydrofuran (THF) was added to dissolve the adhesive. After four hours, 38 ml of hexane containing 0.01% (v/v) hexyl acetate (as an internal standard) was added to the THF solution (volume ratio 5% THF). The container was shaken until the entire dosage unit was dissolved. The sample was centrifuged and was transferred into an HPLC vial. The filtrate was injected into a gas chromatograph with FID detector. Results are shown below.

Average thickness of adhesive polymer matrix: 100 μm
Average composition of adhesive polymer matrix:

| Component: | mg per 15 cm$^2$ patch | wt % |
|---|---|---|
| PVP/VA-S630: | 10.0 | 3.34 |
| DURO TAK 87-4098: | 211.3 | 70.43 |
| Enhancers: | | |
| DMSO: | 24.0 | 8.00 |
| Lauryl lactate: | 25.2 | 8.40 |
| Ethyl lactate: | 4.5 | 1.50 |
| Capric Acid: | 18.0 | 6.00 |
| Hormones: | | |
| Levonorgestrel | 4.7 | 1.57 |
| Ethinyl estradiol | 2.3 | 0.77 |
| TOTAL: | 300.0 | 100.00 |

EXAMPLE 3

Effects of Process Parameters on Final Composition of Skin Permeation Enhancers in the Adhesive Polymer Matrix The effect of THDS fabrication parameters on the final composition of skin permeation enhancers in the adhesive polymer matrix was tested. Four process parameters were varied: drying temperature, drying time, initial coating thickness and the weight percent of total enhancers in the initial formulation. Results are shown in the table below. Each value represents an average of four patches. Values are given in mg/g of adhesive polymer matrix.

TABLE 1

Enhancer Composition in Patches Subjected to Varying Process Parameters

| Grp # | Drying Temp. (° C.) | Drying Time (min) | Coating Thickness (mm) | Initial Enhancer (Wt %) | Ethyl Lactate | DMSO | Capric Acid | Lauryl Lactate |
|---|---|---|---|---|---|---|---|---|
| 1 | 40 | 15 | 600 | 20.77 | 35.28 ± 1.17 | 224.84 ± 6.54 | 76.24 ± 1.12 | 99.78 ± 6.48 |
| 2 | 50 | 15 | 600 | 20.77 | 25.10 ± 0.74 | 158.04 ± 6.33 | 84.27 ± 2.56 | 115.57 ± 3.84 |
| 3 | 60 | 15 | 600 | 20.77 | 17.74 ± 0.92 | 111.12 ± 3.19 | 90.07 ± 1.52 | 124.79 ± 1.60 |
| 4 | 70 | 15 | 600 | 20.77 | 11.31 ± 0.78 | 53.32 ± 4.47 | 91.88 ± 4.17 | 130.17 ± 4.27 |
| 5 | 80 | 15 | 600 | 20.77 | 7.55 ± 0.41 | 27.17 ± 4.23 | 92.87 ± 4.88 | 138.30 ± 4.27 |
| 6 | 100 | 15 | 600 | 20.77 | 2.23 ± 0.21 | 2.00 ± 0.21 | 58.48 ± 1.72 | 126.70 ± 2.97 |
| 7 | 60 | 5 | 600 | 20.77 | 37.52 ± 2.45 | 234.32 ± 7.67 | 74.14 ± 2.38 | 108.28 ± 2.79 |
| 8 | 60 | 10 | 600 | 20.77 | 21.00 ± 0.46 | 154.11 ± 4.52 | 83.33 ± 2.23 | 115.07 ± 3.55 |
| 3 | 60 | 15 | 600 | 20.77 | 17.74 ± 0.92 | 111.12 ± 3.19 | 90.07 ± 1.52 | 124.79 ± 1.60 |
| 9 | 60 | 20 | 600 | 20.77 | 10.73 ± 0.55 | 74.64 ± 4.05 | 91.98 ± 1.76 | 136.25 ± 2.68 |
| 10 | 60 | 25 | 600 | 20.77 | ND | 17.21 ± 1.16 | 107.94 ± 5.61 | 203.79 ± 8.46 |
| 11 | 60 | 15 | 300 | 20.77 | 5.38 ± 0.61 | 47.51 ± 3.29 | 91.85 ± 1.73 | 135.87 ± 4.09 |
| 12 | 60 | 15 | 400 | 20.77 | 5.07 ± 0.35 | 42.34 ± 4.51 | 92.77 ± 2.18 | 166.10 ± 2.17 |
| 13 | 60 | 15 | 500 | 20.77 | 6.54 ± 0.27 | 76.17 ± 2.86 | 94.04 ± 5.31 | 154.79 ± 9.54 |
| 3 | 60 | 15 | 600 | 20.77 | 17.74 ± 0.92 | 111.12 ± 3.19 | 90.07 ± 1.52 | 124.79 ± 1.60 |
| 14 | 60 | 15 | 700 | 20.77 | 18.92 ± 1.06 | 137.58 ± 5.47 | 82.72 ± 3.64 | 120.69 ± 5.44 |
| 15 | 60 | 15 | 800 | 20.77 | 21.63 ± 0.42 | 142.27 ± 3.28 | 78.42 ± 1.19 | 110.09 ± 1.12 |
| 16 | 60 | 15 | 600 | 7.15 | ND | ND | 50.24 ± 10.64 | ND |
| 17 | 60 | 15 | 600 | 11.98 | 7.64 ± 0.21 | 56.58 ± 1.37 | 60.23 ± 0.52 | 59.65 ± 1.36 |
| 18 | 60 | 15 | 600 | 16.81 | 10.35 ± 1.37 | 76.71 ± 10.58 | 69.35 ± 12.03 | 94.64 ± 12.73 |
| 3 | 60 | 15 | 600 | 20.77 | 17.74 ± 0.92 | 111.12 ± 3.19 | 90.07 ± 1.52 | 124.79 ± 1.60 |
| 19 | 60 | 15 | 600 | 26.47 | 21.63 ± 0.42 | 142.27 ± 3.28 | 78.42 ± 1.19 | 110.09 ± 1.12 |
| 20 | 80 | 5 | 600 | 20.77 | 13.35 ± 1.13 | 92.23 ± 7.15 | 68.15 ± 1.34 | 113.23 ± 4.28 |
| 21 | 80 | 10 | 600 | 20.77 | 4.95 ± 0.41 | 40.69 ± 4.48 | 78.77 ± 1.98 | 110.59 ± 1.73 |
| 5 | 80 | 15 | 600 | 20.77 | 7.55 ± 0.41 | 27.17 ± 4.23 | 92.87 ± 4.88 | 138.30 ± 4.27 |
| 22 | 80 | 20 | 600 | 20.77 | 0.29 ± 0.58 | 7.89 ± 1.35 | 67.02 ± 6.25 | 108.45 ± 6.55 |

EXAMPLE 4

Clinical Study

An open-label, dose-response, 4-cycle, multi-center study was conducted to determine the levels LNG, EE, progesterone, LH and estradiol after treatment with a THDS produced according to the protocols set forth in Example 1. The objectives of the clinical study were: (1) to determine the safety of a seven day LNG/EE THDS in healthy ovulatory women; (2) to determine the serum levels of LNG and EE after treatment with an LNG/EE THDS; (3) to determine the serum levels of progesterone as an indicator of ovulation after treatment with an LNG/EE THDS; and (4) to determine the levels of LH and estradiol after treatment with an LNG/EE THDS.

The serum levels of LNG and EE were determined three times weekly throughout the study. The serum levels of LH, estradiol, and progesterone were also determined three times weekly throughout the study. Levels of progesterone equal to or greater than 3 ng/ml were taken as presumptive evidence of ovulation. Cycle control was assessed by determining the incidence of spotting, breakthrough bleeding, withdrawal bleeding and amenorrhea from diary cards. Spotting was defined as a light flow that required the use of up to two sanitary protective pads. Breakthrough bleeding was defined as a heavier flow that necessitated the use of three or more sanitary protection pads. Spotting and/or breakthrough bleeding was defined as any bleeding or spotting that occurred between days 5-21 except bleeding that began prior to day 21 and continued past that date. Amenorrhea was defined as the absence of any bleeding during the entire 28 day cycle. Withdrawal bleeding was defined as any spotting or bleeding of more than one day in duration on or after day 22 (during the 7-day period in which no THDS was applied.).

Safety was assessed by the adverse events that were described by the patient without prompting. Changes in physical examinations, vital signs, and laboratory functions were also determined.

LNG serum samples were analyzed by RIA and EE serum samples were analyzed by gas chromatography/mass spectrometry to determine the subjects' serum levels of those hormones periodically during the study. Preliminary results are shown in the table below, for patches of 15, 17.5 and 20 $cm^2$, respectively, for the formula.

TABLE 2

Serum Levels of Levonorgestrel and Ethinyl Estradiol in Clinical Trial Test Subjects During Four Cycles of Administration of THDS

| | | Levonorgestrel (pg/ml) | | | Ethinyl Estradiol (pg/ml) | | |
|---|---|---|---|---|---|---|---|
| Cycle | Day | 15 $cm^2$ | 17.5 $cm^2$ | 20 $cm^2$ | 15 $cm^2$ | 17.5 $cm^2$ | 20 $cm^2$ |
| 1 | 1 | 2.00 (N = 11) | 2.00 (N = 11) | 2.00 (N = 17) | 1.08 ± 0.21 (N = 10) | 1.03 ± 0.16 (N = 11) | 1.19 ± 0.41 (N = 17) |
| | 3 | 844.71 ± 724.50 (N = 13) | 1001.01 ± 634.24 (N = 11) | 920.73 ± 525.40 (N = 16) | 30.48 ± 9.56 (N = 13) | 41.77 ± 21.88 (N = 11) | 42.73 ± 32.94 (N = 16) |

TABLE 2-continued

Serum Levels of Levonorgestrel and Ethinyl Estradiol in Clinical Trial Test Subjects During Four Cycles of Administration of THDS

| | | Levonorgestrel (pg/ml) | | | Ethinyl Estradiol (pg/ml) | | |
|---|---|---|---|---|---|---|---|
| Cycle | Day | 15 cm$^2$ | 17.5 cm$^2$ | 20 cm$^2$ | 15 cm$^2$ | 17.5 cm$^2$ | 20 cm$^2$ |
| | 8 | 1054.45 ± 642.21 (N = 11) | 1249.42 ± 626.77 (N = 12) | 1019.48 ± 521.57 (N = 18) | 21.06 ± 6.50 (N = 11) | 32.78 ± 21.45 (N = 12) | 27.65 ± 24.10 (N = 19) |
| | 10 | 1589.84 ± 565.74 (N = 12) | 2052.75 ± 1100.75 (N = 13) | 2112.87 ± 693.04 (N = 12) | 30.88 ± 10.71 (N = 12) | 46.46 ± 23.52 (N = 13) | 39.79 ± 9.62 (N = 12) |
| | 15 | 1222.61 ± 399.92 (N = 13) | 1664.76 ± 462.71 (N = 11) | 1392.26 ± 711.44 (N = 17) | 24.35 ± 10.21 (N = 11) | 38.50 ± 18.62 (N = 10) | 23.19 ± 10.45 (N = 16) |
| | 17 | 2574.70 ± 1461.29 (N = 12) | 2644.92 ± 1506.96 (N = 9) | 2460.92 ± 1185.72 (N = 14) | 41.05 ± 13.17 (N = 11) | 60.78 ± 34.20 (N = 10) | 46.35 ± 23.74 (N = 16) |
| | 22 | 1460.10 ± 574.76 (N = 12) | 1898.69 ± 843.73 (N = 12) | 1616.14 ± 1033.81 (N = 17) | 22.27 ± 9.82 (N = 12) | 41.54 ± 18.81 (N = 13) | 29.73 ± 23.84 (N = 19) |
| 2 | 1 | 923.77 ± 1184.97 (N = 7) | 408.51 ± 683.41 (N = 8) | 254.44 ± 418.96 (N = 8) | 18.46 ± 18.42 (N = 7) | 9.25 ± 8.19 (N = 8) | 11.89 ± 17.09 (N = 8) |
| | 3 | 1223.70 ± 277.64 (N = 5) | 1820.44 ± 1084.88 (N = 9) | 1513.82 ± 601.49 (N = 7) | 35.51 ± 14.05 (N = 6) | 64.65 ± 25.22 (N = 8) | 39.70 ± 15.82 (N = 7) |
| | 8 | 929.07 ± 126.26 (N = 6) | 1442.98 ± 689.62 (N = 9) | 1397.46 ± 815.37 (N = 7) | 28.44 ± 16.11 (N = 7) | 40.24 ± 19.43 (N = 9) | 36.19 ± 23.06 (N = 7) |
| | 10 | 1904.12 ± 583.88 (N = 6) | 2433.64 ± 1092.91 (N = 9) | 3016.86 ± 1871.56 (N = 7) | 36.49 ± 13.86 (N = 6) | 58.67 ± 33.72 (N = 9) | 49.12 ± 22.02 (N = 7) |
| | 15 | 1454.02 ± 597.78 (N = 7) | 1545.99 ± 639.46 (N = 9) | 1940.63 ± 1118.38 (N = 6) | 26.90 ± 9.54 (N = 7) | 39.57 ± 22.80 (N = 9) | 25.15 ± 8.81 (N = 6) |
| | 17 | 2674.99 ± 1335.90 (N = 7) | 3177.80 ± 1379.79 (N = 7) | 2863.36 ± 1556.44 (N = 7) | 40.23 ± 14.93 (N = 7) | 65.79 ± 33.65 (N = 7) | 41.82 ± 17.90 (N = 7) |
| | 22 | 1403.37 ± 413.89 (N = 7) | 1811.11 ± 856.59 (N = 9) | 2071.22 ± 1161.46 (N = 7) | 27.32 ± 18.59 (N = 7) | 36.49 ± 21.38 (N = 9) | 26.11 ± 13.85 (N = 6) |
| 3 | 1 | 62.00 | 2.00 | 97.38 ± 66.64 (N = 4) | 5.63 | 0.98 | 5.92 ± 3.52 (N = 4) |
| | 3 | 467.00 | 2124.11 | 1878.00 ± 506.67 (N = 4) | 19.38 | 80.24 | 43.15 ± 15.74 (N = 4) |
| | 8 | 362.41 ± 164.88 (N = 2) | 1424.82 | 2026.13 ± 943.19 (N = 4) | 18.89 ± 20.14 (N = 2) | 31.98 | 33.37 ± 13.09 (N = 4) |
| | 10 | 1084.63 ± 266.77 (N = 2) | 3274.46 | 3780.44 ± 1783.33 (N = 4) | 41.77 ± 15.76 (N = 2) | 101.75 | 52.07 ± 12.37 (N = 4) |
| | 15 | 937.32 ± 176.32 (N = 2) | 1775.66 | 2500.13 ± 752.94 (N = 4) | 34.20 ± 17.42 (N = 2) | 43.61 | 27.72 ± 6.83 (N = 4) |
| | 17 | 947.81 ± 978.37 (N = 2) | 7175.00 | 2911.94 ± 953.73 (N = 4) | 31.06 ± 34.20 (N = 2) | 87.21 | 25.34 ± 10.93 (N = 4) |
| | 22 | 919.69 ± 116.95 (N = 2) | 2274.46 | 2175.81 ± 1273.49 (N = 4) | 22.17 ± 4.83 (N = 2) | 34.89 | 29.20 ± 12.24 (N = 4) |
| 4 | 1 | 49.00 | ND | 44.13 ± 59.57 (N = 2) | 4.38 | ND | 3.30 ± 3.29 (N = 2) |
| | 8 | 576.00 | ND | 1559.75 ± 392.09 (N = 2) | 16.88 | ND | 34.51 |
| | 15 | 940.00 | ND | 2634.88 ± 1458.23 (N = 2) | 10.63 | ND | 27.16 ± 4.91 (N = 2) |
| | 22 | 1283.00 | | 2588.50 ± 1093.89 (N = 2) | 17.50 | ND | 23.01 ± 3.70 (N = 2) |

The present invention is not limited to the embodiments described and exemplified above, but is capable of variation and modification within the scope of the appended claims.

What is claimed is:

1. A transdermal hormone delivery system comprising a backing layer and an adhesive polymer matrix affixed to the backing layer, wherein the adhesive polymer matrix comprises:
   (a) an adhesive polymer;
   (b) a humectant;
   (c) a combination of skin permeation enhancing agents consisting essentially of, on a final percentage by weight of the adhesive polymer matrix after fabrication of the system, from about 4% to about 12% dimethyl sulfoxide; from about 4.2% to about 12.6% a fatty ($C_8$-$C_{20}$) alcohol ester of lactic acid; from about 0.7% to about 2.3% lower ($C_1$-$C_4$) alkyl ester of lactic acid; and from about 3% to about 9% capric acid;
   (d) a progestin; and
   (e) an estrogen.

2. The transdermal delivery system of claim 1, wherein the adhesive polymer is a polyacrylate copolymer, a polyisobutylene or a silicone adhesive.

3. The transdermal delivery system of claim 2, wherein the polyacrylate copolymer comprises a 2-ethylhexyl acrylate monomer.

4. The transdermal delivery system of claim 3, wherein the polyacrylate copolymer further comprises about 3 to 60% w/w vinyl acetate.

5. The transdermal delivery system of claim 1, wherein the humectant comprises polyvinylpyrrolidone.

6. The transdermal delivery system of claim 5, wherein the humectant comprises a polyvinylpyrrolidone copolymer.

7. The transdermal delivery system of claim 6, wherein the humectant is a polyvinylpyrrolidone/vinyl acetate copolymer.

8. The transdermal delivery system of claim 7, wherein the polyvinylpyrrolidone is formulated in an amount of about 60% w/w and the vinyl acetate is formulated in an amount of about 40% w/w in the polyvinylpyrrolidone/vinyl acetate copolymer.

9. The transdermal delivery system of claim 1, wherein the fatty alcohol ester of lactic acid is lauryl lactate.

10. The transdermal delivery system of claim 1, wherein the lower alkyl ester of lactic acid is ethyl lactate.

11. The transdermal delivery system of claim 1, wherein the progestin is levonorgestrel.

12. The transdermal delivery system of claim 1, wherein the estrogen is ethinyl estradiol or 17 β-estradiol.

13. The transdermal delivery system of claim 11, which, when applied to the skin of a human, once each week, consecutively over a period of three or more weeks, deliver in vivo an average serum concentration of over 1000 pg/ml of levonorgestrel.

14. The transdermal delivery system of claim 1, wherein the adhesive polymer matrix comprises about 12% to about 36% by weight of the combination of skin permeation enhancing agents.

15. The transdermal delivery system of claim 1, wherein the adhesive polymer matrix comprises about 18% to about 30% by weight of the combination of skin permeation enhancing agents.

16. The transdermal delivery system of claim 1, wherein the adhesive polymer matrix comprises about 21% to about 27% by weight of the combination of skin permeation enhancing agents.

17. The transdermal delivery system of claim 1, wherein the adhesive polymer matrix is formulated by combining the adhesive polymer, the humectant, the progestin, the estrogen, and about 10% to about 30% by weight of the combination of skin permeation enhancing agents.

18. The transdermal delivery system of claim 1, wherein the adhesive polymer matrix is formulated by combining the adhesive polymer, the humectant, the progestin, the estrogen, and about 13% to about 27% by weight of the combination of skin permeation enhancing agents.

19. The transdermal delivery system of claim 1, wherein the capric acid is present in an amount between about 4% and about 8% by weight of the adhesive polymer matrix.

20. The transdermal delivery system of claim 1, wherein the capric acid is present in an amount between about 5% and about 7% by weight of the adhesive polymer matrix.

21. The transdermal delivery system of claim 1, wherein the dimethyl sulfoxide is present in an amount between about 5% and about 11% by weight of the adhesive polymer matrix.

22. The transdermal delivery system of claim 1, wherein the dimethyl sulfoxide is present in an amount between about 6% and about 10% by weight of the adhesive polymer matrix.

23. The transdermal delivery system of claim 1, wherein the fatty ($C_8$-$C_{20}$) alcohol ester of lactic acid is present in an amount between about 5.2% and about 11.6% by weight of the adhesive polymer matrix.

24. The transdermal delivery system of claim 1, wherein the fatty ($C_8$-$C_{20}$) alcohol ester of lactic acid is present in an amount between about 6.2% and about 10.6% by weight of the adhesive polymer matrix.

25. The transdermal delivery system of claim 1, wherein the lower ($C_1$-$C_4$) alkyl ester of lactic acid is present in an amount between about 1.0% and about 2.0% by weight of the adhesive polymer matrix.

26. The transdermal delivery system of claim 1, wherein the lower ($C_1$-$C_4$) alkyl ester of lactic acid is present in an amount between about 1.2% and about 1.8% by weight of the adhesive polymer matrix.

* * * * *